United States Patent [19]

Adrey et al.

[11] Patent Number: 5,139,522

[45] Date of Patent: Aug. 18, 1992

[54] FEMORAL HIP PROSTHESIS

[76] Inventors: José Adrey, 43, Faubourg St. Jaumes, 34000 Montpellier; Daniel Berteaux, 64bis, Rue de Fossés, 45400 Fleury les Aubrais; Christian Goalard, 43, Faubourg St. Jaumes, 34000 Montpellier; Alain Gueret, 29-31 Rue Thiers, 88000 Epinal; Georges Hamon, Rue Henri Barbusse, 59880 Saint Saulve; Christian Nourissat, 75 Rue Général Giraud, 42308 Roannes Cedex, all of France

[21] Appl. No.: 429,921

[22] Filed: Oct. 30, 1989

[30] Foreign Application Priority Data

Nov. 2, 1988 [FR] France ................... 88.14277

[51] Int. Cl.⁵ .............................................. A61F 2/32
[52] U.S. Cl. .................................................... 623/23
[58] Field of Search ................................. 623/16-23

[56] References Cited

U.S. PATENT DOCUMENTS

| 4,223,412 | 9/1980 | Aoyagi et al. | 623/76 |
| 4,530,116 | 7/1985 | Frey | 623/23 |
| 4,670,015 | 6/1987 | Freeman | 623/23 |

Primary Examiner—David J. Isabella
Attorney, Agent, or Firm—Peter C. Richards; Lawrence C. Akers; Raymond W. Augustin

[57] ABSTRACT

A hip joint femoral prosthesis has a rod, the proximal end of which has a cross-section of oval shape and a surface area increasing towards the proximal end. At least one wall of the proximal end includes alveoli therein hollowed out so as to present a maximum depth on their side towards the proximal end. The alveoli are of a circular or semi-circular shape and intersect, thereby providing a surface which improves the stability and anchoring of the prosthesis into the femur.

7 Claims, 6 Drawing Sheets

FEMORAL HIP PROSTHESIS

BACKGROUND OF THE INVENTION

This invention relates to a hip joint femoral prosthesis. More particularly, it relates to a prosthesis having fish scale depressions on the proximal end to enhance fixation after implantation, particularly in a non-cemented hip.

Femoral hip joint prostheses which have at their distal end a rod to be inserted into the femur medullary canal, and at the other end a neck made integral with an element for accommodating a femur head of spherical shape, are well known. Such prostheses have a shape to facilitate their introduction and positioning into a femoral intramedullary canal which has been previously reamed out by a surgeon. These prostheses must possess an outer surface permitting efficient regrowth of the bone tissue. Finally, the prosthesis must, as much as possible, be easily removable without causing any additional damage to the femur, since, obviously, the femur is already damaged to an extent requiring implantation of such a prosthesis.

In order for the femoral components to possess all of these properties, some of which are contradictory, it has already been proposed to give the rods a rectilinear shape or a shape presenting various curvatures with a circular or oval cross-section. These components may have a terminal angle that facilitates the introduction into, or the removal from the femur. These rods may also have flutes or serrations present at their periphery to permit better ingrowth of bone tissue; or they may even be coated with a coating layer known to be resorbed in the blood medium such as a hydroxyapatite layer.

However, a femoral component having such a coating thereon, which coating dissolves with time in the bone tissue, has a disadvantage. Due to dissolution of the coating, these components have a tendency to be driven more deeply into the femur. Such a displacement of the prosthesis with respect to the femur or bone in which it is implanted works against the firm anchoring of the latter in the canal.

It has been attempted to remedy this disadvantage by providing, on the walls of the proximal end of the femoral component, raised portions resisting any lowering of the prosthesis into the femur. In particular, these projections may be in the form of ladder steps or horizontal serrations. However, these projections are not entirely satisfactory because, as the area on which they might be made is limited, they fulfill their function only imperfectly.

U.S. Pat. No. 4,530,116 discloses an anchoring shank with a plurality of depressions having an arch-like shape with flanks which taper conically towards the proximal end. These depressions are intended to improve the adhesion between bone cement and the shank.

SUMMARY OF THE INVENTION

The object of this invention is an improvement thereof which permits a more positive anchoring in the bone tissue. This object is achieved by hollowing out depressions or alveoli which exhibit a maximum depth on the proximal side and a minimum depth on the distal side of the rod. These depressions are located at the proximal end of the rod, i.e. the portion of the femoral implant located in the area of the extension of the center line of the neck. The cross-section in this area is usually of an oval shape. In this section of the component, the surface area increases with the distance from the distal portion of the rod and the depressions are formed on at least one of the walls of this oval portion of the rod (usually posterior or anterior). Thus, the area covered by depressions also increases from the distal end to the proximal end of the femoral component.

These alveoli are preferably practically circular or semicircular in shape. They may be disposed in staggered rows of both circular or semi-circular depressions, which may be sufficiently close to one another so that their peripheries intersect and give the aspect of fish scales to the so textured surface.

The alveoli or depressions are preferably formed on both the forward (anterior) and rearward (posterior) walls of the proximal portions of the femoral component, since these walls correspond to those sides of that oval portion of the rod which present, in cross-section, the largest radii of curvature, thus offering the largest lateral surface area. These alveoli may also be formed on the inner or medial wall of the proximal portion of the oval cross-section of the rod.

It is to be noted that the shape of this proximal portion of the rod, i.e. with the oval cross-section having a surface area increasing towards the neck, has the obvious advantage of increasing the lateral surface area of the wall or walls to be covered with alveoli. The shape of this area can be combined with the very shape of the alveoli to place the maximum number thereof on the so offered lateral surface to thus obtain maximum support for the prosthesis in the femur. Such an alveolar structure does not in any manner affect the positioning of the prosthesis in so far as its lodging was previously provided for in the medullar femur canal by the reaming step.

This structure is such as to provide a stable load distribution over all of a significant surface area for support in the bone once the prosthesis has been finally positioned. Therefore, it permits fixation thereof which is such as to resist and limit, in a natural manner, the driving down or the rotation of the prosthesis into the medullar canal. The semicircular or circular shape of the alveoli, in particular the whole of the edge portions comprised therein, increases the stability of the prosthesis due to a better distribution of the forces over large lateral surfaces. The very shape of these depressions also has the advantage of being totally compatible with easy removal of the prosthesis.

In addition to these purely mechanical advantages, the alveoli or depressions formed in the walls of the implant increase the area of the prosthesis in contact with the bone tissue, while leaving such a volume as is necessary for bone regrowth. The alveoli also have the advantage of favoring the reconstitution of the bone tissue, thereby also providing for stability and fixation of the prosthesis into the femur.

Finally, the shape of the alveoli of the present invention is particularly favorable to permit accommodation and adherence of a hydroxyapatite coating which increases and stimulates the osteo-conductive characteristics of the implant.

BRIEF DESCRIPTION OF THE DRAWINGS

This invention will now be described with reference to the attached drawings in which.

DESCRIPTION OF THE PREFERRED EMBODIMENT

Referring to FIGS. 1-6, the prosthesis (generally denoted as 1) comprises a rod or femoral component 2 of elongated shape connected in the intertrochanterian zone to a neck 3 made integral with an element 4 for receiving thereon a femoral head of spherical shape (not shown).

Figure 1:
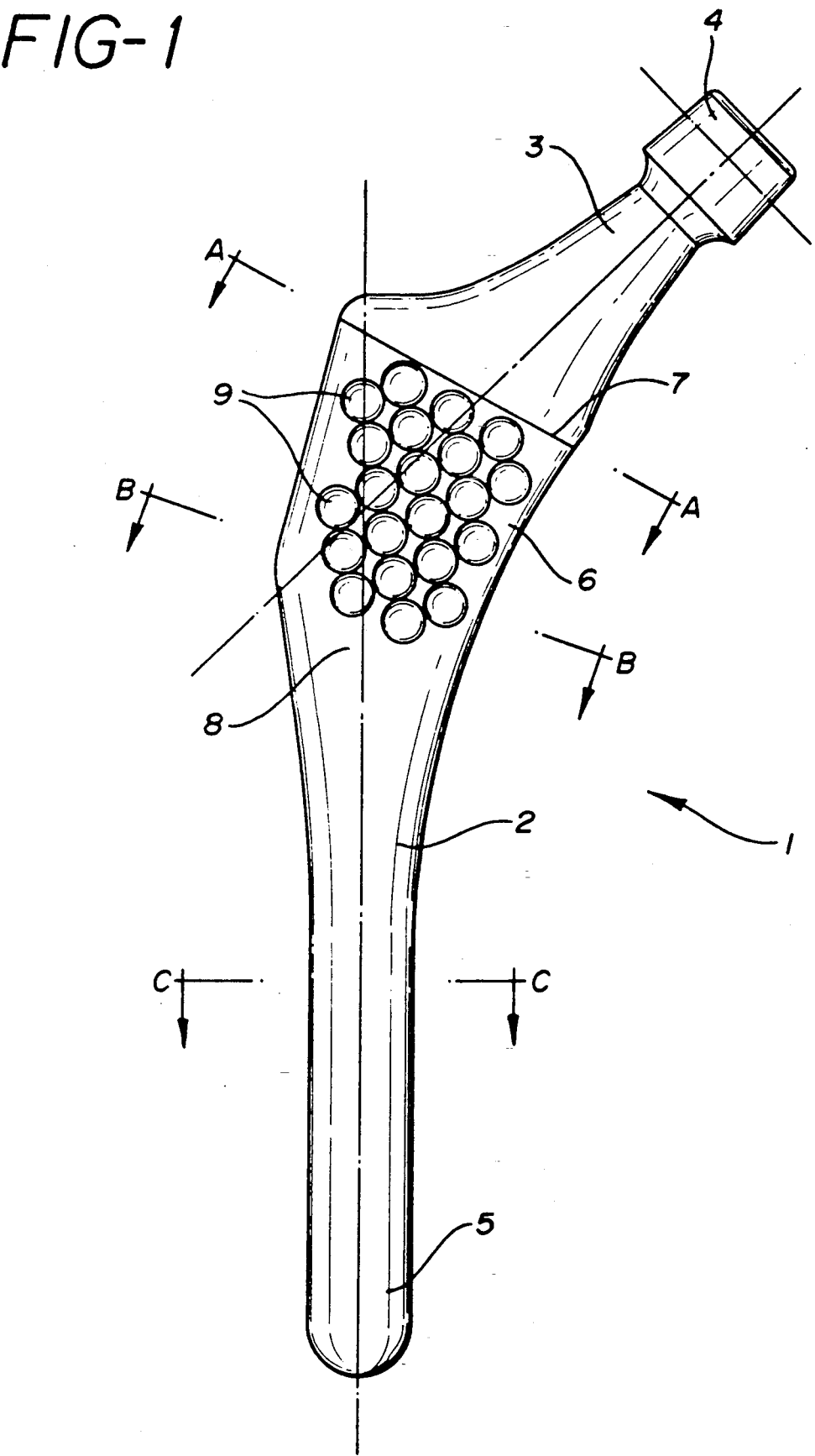
FIG. 1 represents a side view of a first embodiment of a prosthesis according to the invention.
Figure 2:
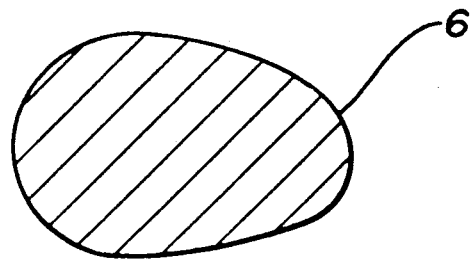
FIGS. 2 to 4 represent cross-sectional views according to lines A—A, B—B and C—C respectively of FIG. 1.
Figure 3:
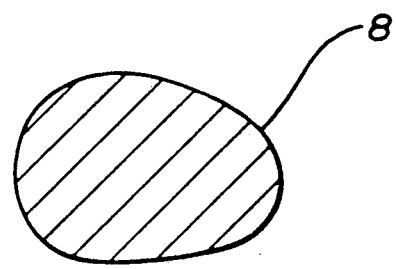
Figure 4:
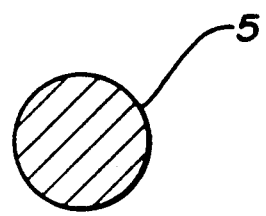

Rod 2 comprises a relatively elongated distal end 5 of circular cross-section as illustrated in FIG. 4, and a relatively short proximal end 6 of oval cross-section, the surface area of which increases towards its proximal end as shown in FIGS. 2 and 3, i.e. as it comes closer to the intertrochanterian zone shown in FIG. 1 by line 7.

The portion of the rod 2 between the intertrochanterian zone 7 and the connecting zone 8 are of oval and circular cross-sections and constitutes the proximal end 6 of the rod. End 6 is located in the extension of the center line of the prosthesis neck.

According to the present invention, this portion of the rod called proximal end 6 is to be covered with alveoli or depressions. According to a first form of embodiment shown in FIGS. 1-6, the forward and rearward lateral walls of such end 6 of the rod include the alveoli thereon.

Figure 5:
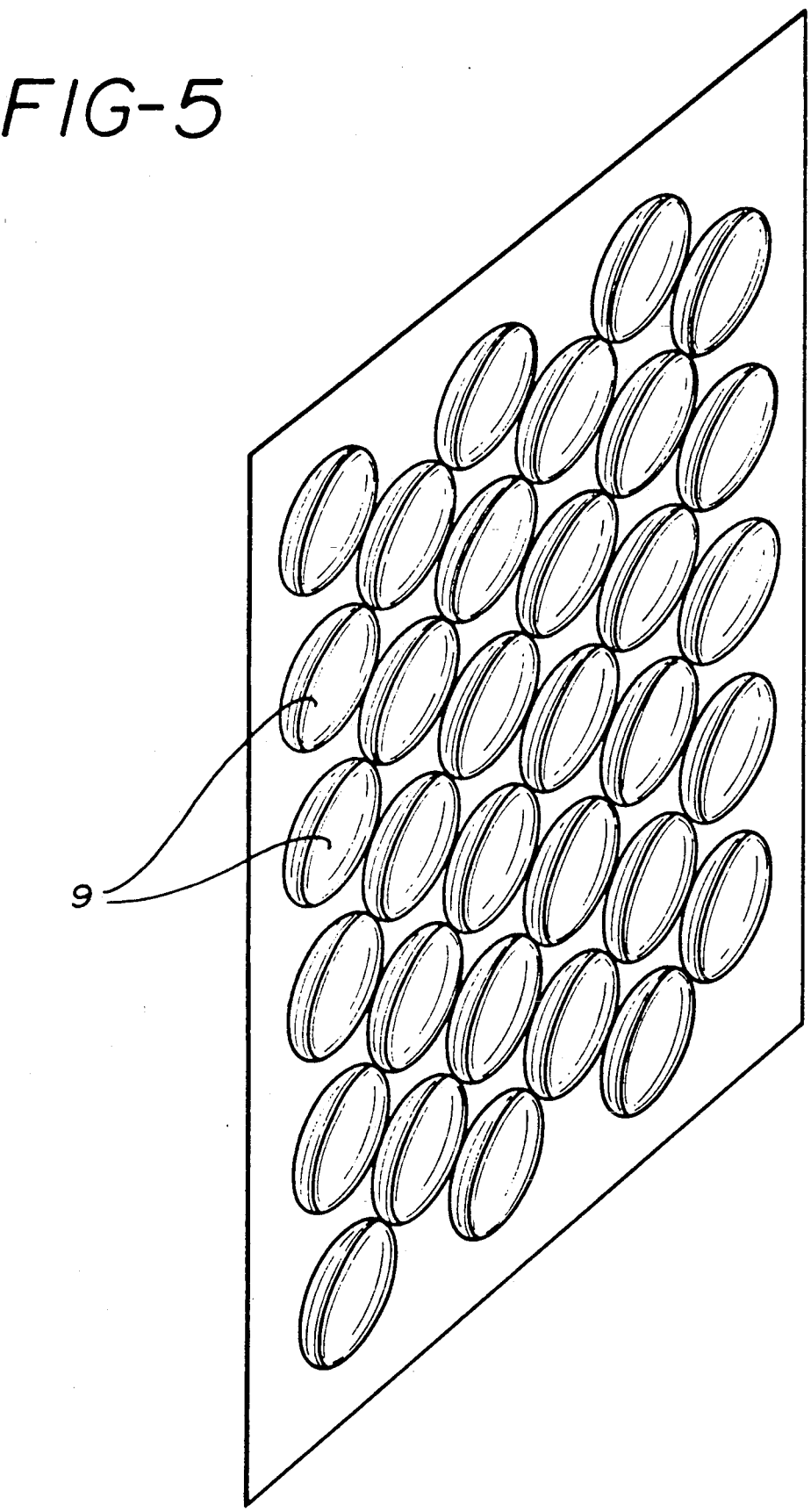
FIGS. 5 and 6 represent, on a much larger scale, respective views in relief and in cross-section of the alveoli of the first form of embodiment.
Figure 6:
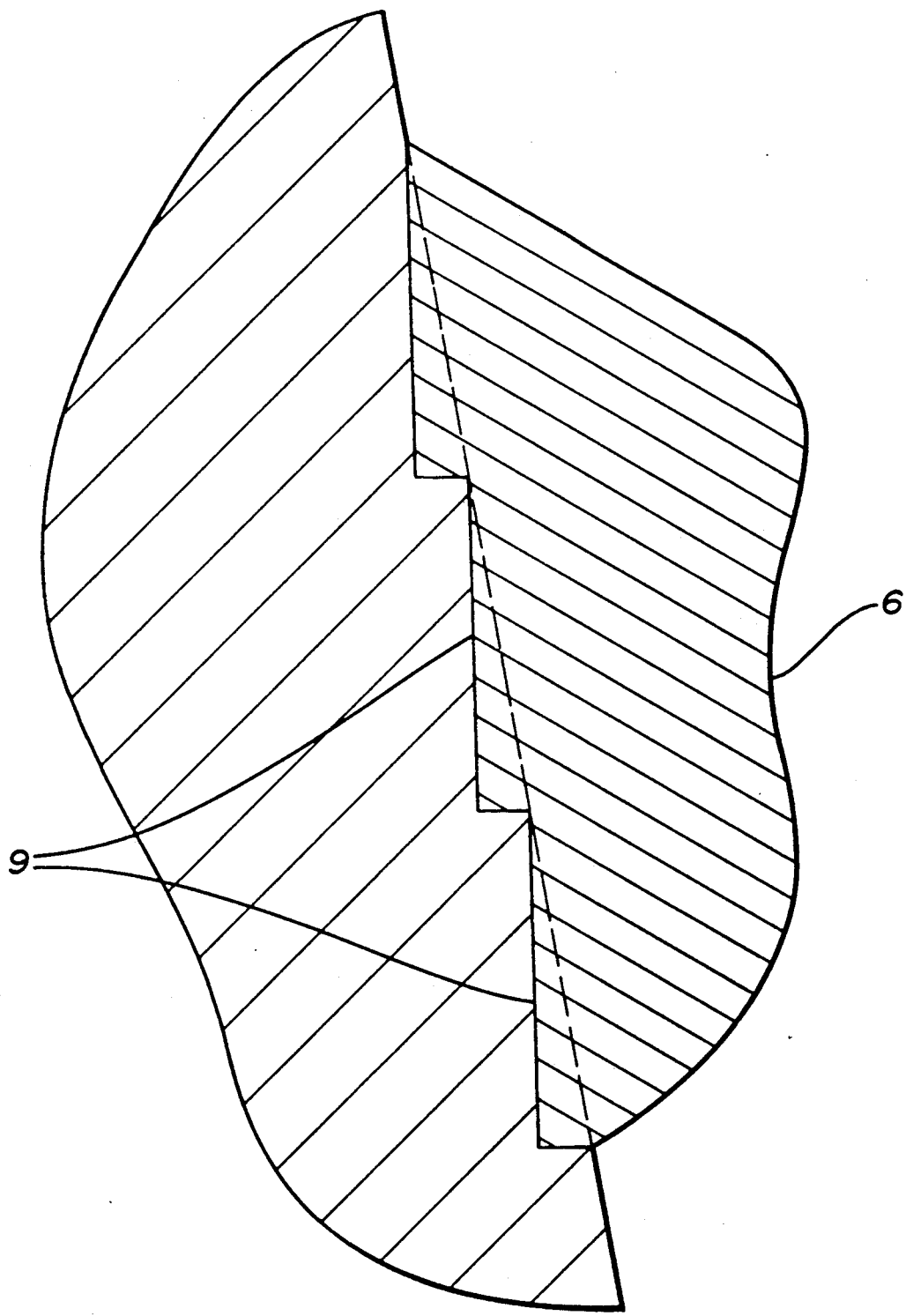

Such alveoli, in the shape of the embodiment shown in FIGS. 1-6, have a circular shape and are distributed in staggered rows on the surface of these two walls in the form of tangent or intersecting circles. As shown schematically in FIGS. 5 and 6, the alveoli 9 are formed by hollowing out or cutting planar circular cavities such that the depth of the cavities is maximum on the proximal end of the rod or stem and at an angle with respect to the axial center line of distal end 5 and absent or flush on the opposite (distal) side. Thus, as depicted in FIGS. 5 and 6, the deeper end of each alveoli are generally proximal and angled with respect to the axia of stem 5. The proximal direction is to the left side of FIG. 5 and towards the bottom of FIG. 6.

Figure 7:
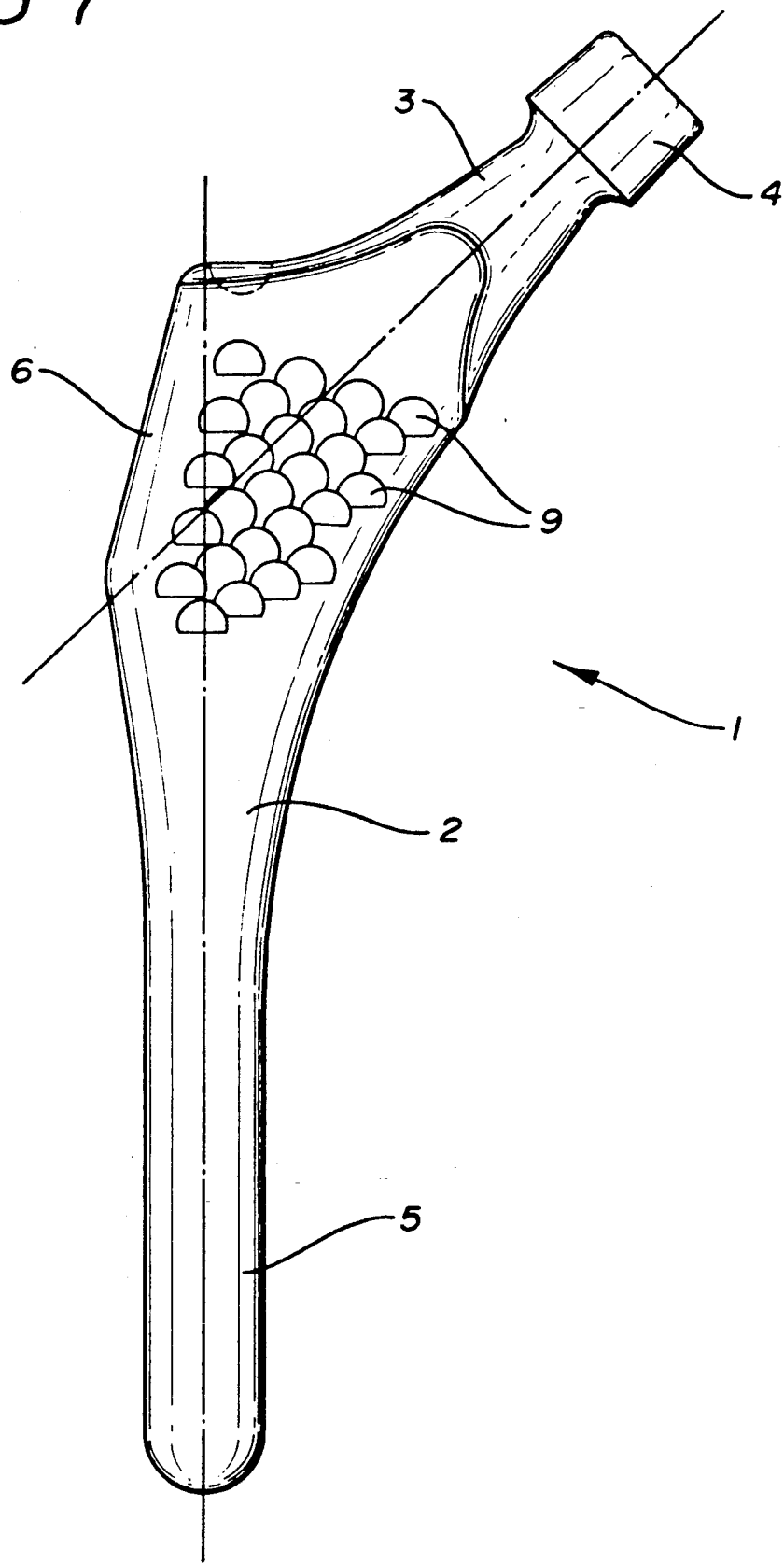
FIG. 7 represents a side view of a second embodiment of a prosthesis according to the invention.
Figure 8:
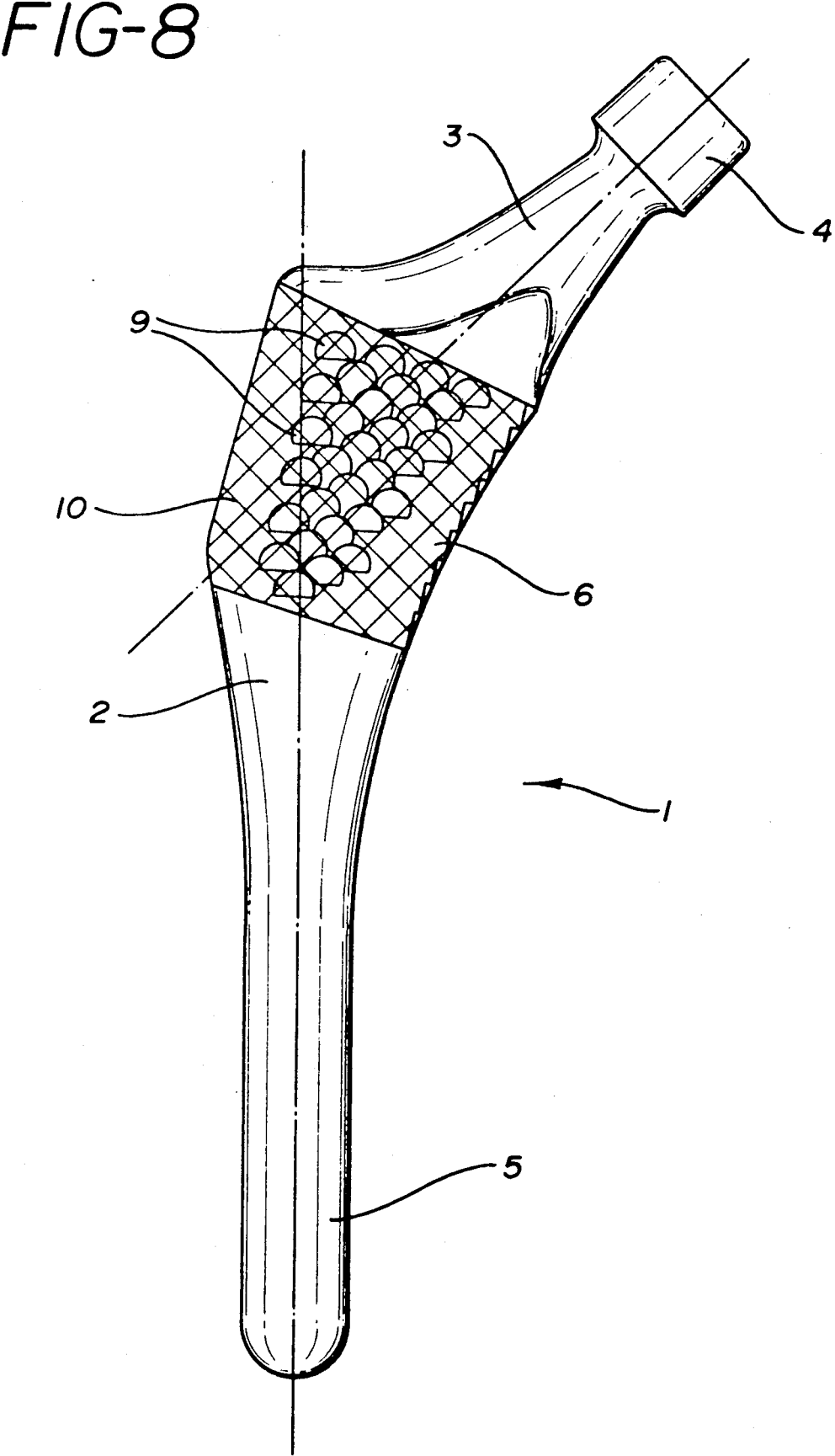
FIG. 8 represents a lateral view of a third embodiment of the invention.

The prosthesis shown in FIG. 7 differs from that shown in FIGS. 1-6 in that the alveoli are practically semi-circular and so close to one another that their circular peripheries intersect to a predetermined extent, thus giving the aspect of fish scales thereto. The prosthesis of FIG. 8 differs from the form of embodiment of FIG. 7 by the application of a hydroxyapatite coating shown by the cross-hatched area 10 on all the alveolated portions 6 of the rod. This same FIG. 8 also shows that not only the forward and the rearward walls, but also the inner medial wall of the proximal end 6 of the femoral component may include alveoli thereon.

The various prostheses according to the invention can be easily manufactured with the alveolated wall(s) integrally formed thereon. The alveolated prostheses, so obtained in rough form from forging, can then be covered with a hydroxyapatite layer. All the alveoli of the alveolated wall(s) of one and the same prosthesis have preferably the same dimensions.

As mentioned previously, the alveoli or depressions according to the invention are preferably of a practically circular or semi-circular shape. The alveolus diameter is, in view of the usual dimensions of the femoral prostheses, generally comprised between 3 and 7 mm, preferably 5 mm. The maximum hollowed out depth of the alveolus or depressions in the proximal end of the rod is generally between 0.3 and 0.7 mm, preferably 0.5 mm. The angle included between the normal directions to the wall and the plane of the circular bottom of an alveolus or depression is generally comprised between 5 and 20°, preferably between 10° and 15°.

Alveoli with these dimensional characteristics have shown to be satisfactory on femoral prostheses having a length of the alveolated portion of the rod as measured along the center line of the neck between 2 and 5 cm.

While several examples of the present invention have been described, it is obvious that many changes and modifications may be made thereunto, without departing the spirit and scope of the invention.

We claim:

1. A hip joint femoral prosthesis comprising at its distal end a stem extending along a longitudinal axis for insertion into the femur medullar canal and at its other end a neck made integral with an element for accommodating a head of spherical form thereon, said prosthesis comprising:

an outer bone contacting surface area on at least one of a medial, lateral anterior or posterior sides of the prosthesis at the proximal end of said stem, at least one of the medial, lateral, anterior or posterior sides of said proximal portion of the stem including a plurality of adjacent alveoli formed thereon, said alveoli hollowed out so as to present a maximum depth on the proximal end and a minimum depth on the distal end, said alveoli having outer peripheries of a substantially at least semi-circular shape with the apex of each semi-circle, offset at an angle with respect to the stem axis and are distributed in rows in such a close relationship that said semi-circular peripheries of at least two of said adjacent alveoli mutually intersect.

2. A prosthesis according to claim 1, wherein the outer bone contacting surfaces of the proximal portion of the stem have alveoli formed on the anterior, posterior, medial and lateral sides thereof.

3. A prosthesis according to claim 1, wherein the alveoli are distributed in staggered rows on the anterior and posterior sides of said outer surface.

4. A prosthesis according to claim 1, wherein all the alveoli of the outer surface have the same dimensions.

5. A prosthesis according to claim 1, wherein said outer bone contacting surface of the stem is covered with an outer coating of hydroxyapatite.

6. A prosthesis according to claim 1, wherein the alveoli have a diameter of between 3 and 7 mm, and extend into the porosthesis from said outer surface a maximum depth at their apex, said depth being between 0.3 and 0.7 mm, and in that the angle included between the normal direction to the outer surface and to the plane formed by the circular bottom of an alveolus is between 5° and 20°.

7. A prosthesis according to claim 1, wherein the length of the alveolated proximal portion of the stem as measured along the longitudinal center line of the proximal portion is between 2 and 5 cm.

* * * * *